(12) United States Patent
Christmann et al.

(10) Patent No.: US 7,381,712 B2
(45) Date of Patent: Jun. 3, 2008

(54) IN VIVO TRANSFECTION IN AVIANS

(75) Inventors: Leandro Christmann, Watkinsville, GA (US); Markley C. Leavitt, Watkinsville, GA (US); Dawn M. Eberhardt, Athens, GA (US); Timalynn M. Matthews, Bogart, GA (US)

(73) Assignee: AviGenics, Inc., Athens, GA (US)

( * ) Notice: Subject to any disclaimer, the term of this patent is extended or adjusted under 35 U.S.C. 154(b) by 299 days.

(21) Appl. No.: 10/842,606

(22) Filed: May 10, 2004

(65) Prior Publication Data

US 2004/0226057 A1  Nov. 11, 2004

Related U.S. Application Data

(63) Continuation-in-part of application No. 10/790,455, filed on Mar. 1, 2004, now abandoned.

(60) Provisional application No. 60/469,527, filed on May 9, 2003.

(51) Int. Cl.
- A01N 43/04 (2006.01)
- C12P 21/00 (2006.01)
- A01K 67/027 (2006.01)
- C12N 15/00 (2006.01)

(52) U.S. Cl. .................. 514/44; 800/4; 800/7; 800/19; 800/21

(58) Field of Classification Search .................. 800/21, 800/19, 4, 7; 514/44
See application file for complete search history.

(56) References Cited

U.S. PATENT DOCUMENTS

| | | | |
|---|---|---|---|
| 4,997,763 A | 3/1991 | Hughes et al. | |
| 5,011,780 A | 4/1991 | Perry | |
| 5,162,215 A | 11/1992 | Bosselman et al. | |
| 5,175,384 A | 12/1992 | Krimpenfort et al. | |
| 5,340,740 A | 8/1994 | Petitte et al. | |
| 5,656,479 A | 8/1997 | Petitte et al. | |
| 6,027,722 A | 2/2000 | Hodgson | |
| 6,730,822 B1 | 5/2004 | Ivarie et al. | |
| 6,808,925 B2 * | 10/2004 | Calos | 435/462 |
| 6,825,396 B2 * | 11/2004 | MacArthur | 800/19 |
| 2002/0108132 A1 | 8/2002 | Rapp | |
| 2003/0126628 A1 | 7/2003 | Harvey et al. | |
| 2003/0126629 A1 | 7/2003 | Rapp et al. | |
| 2003/0177516 A1 | 9/2003 | Horseman et al. | |
| 2004/0210954 A1 | 10/2004 | Harvey et al. | |
| 2004/0255345 A1 | 12/2004 | Rapp et al. | |

FOREIGN PATENT DOCUMENTS

| | | |
|---|---|---|
| WO | WO 90/11355 | 10/1990 |
| WO | WO 97/47739 | * 12/1997 |
| WO | WO 99/10505 | 3/1999 |

OTHER PUBLICATIONS

Naito (J. Poultry Sci., Oct. 2002, vol. 39, p. 292-301).*
Sano (J. Poultry Sci., Oct. 2003, vol. 40, p. 319-323).*
Davis (Bio/Technology, Feb. 1991, vol. 9, p. 165-169).*
Mohammed (1998, Immunotechnology, vol. 4, p. 115-125).*
Gordon, et al., Production of Human Tissue Plasminogen Activator in Transgenic Mouse Milk; 1987, *Biotechnology*; 5:1183-1187.
Wilmut, et al., Methods of Gene Transfer and Their Potential Use to Modify Milk Composition, 1990, *Theriogenology*; 33:113-123.
Song, et al., Hydrodynamics-Based Transfection: Simple and Efficient Method for Introducing and Expressing Transgenes in Animals by Intravenous Injection of DNA, 2002, *Methods in Enzymology*; 346: 92-105.
Budker, et al., The efficient expression of intravascularly delivered DNA in rat muscle, 1998,*Gene Therapy*; 5: 272-276.
Heller, et al., In vivo gene electroinjection and expression in rat liver; 1996, *FEBS Letters*; 389:225-228.
Koeberl, et al., Persistent expression of human clotting factor IX from mouse liver after intravenous injection of adeno-associated virus vectors; 1997, *Proc. Natl. Acad. Sci. USA*; 94:1426-1431.
Liu, et al., Hydrodynamics-based transfection in animals by systemic administration of plasmid DNA; 1999, *Gene Therapy*; 6:1258-1266.
Maruyama, et al., Continuous Erythropoietin Delivery by Muscle-Targeted Gene Transfer Using in Vivo Electroporation; 2000, *Human Gene Therapy*; 11:429-437.
Mir, et al., High-efficiency gene transfer into skeletal muscle mediated by electric pulses; 1999, *Proc. Natl. Acad. Sci. USA*, 96:4262-4267.
Oshima, et al., Targeted gene transfer to corneal endothelium in vivo by electric pulse; 1985, *Gene Therapy*, 5:1347-1354
Rols, et al., In vivo electrically mediated protein and gene transfer in murine melanoma; 1998, *Nature Biotechnology*, 16:168-171.
Suzuki, et al., Direct gene transfer into rat liver cells by in vivo electroporation; 1998, *FEBS Letters*; 425:436-440.
Türkay, et al., Intrauterine gene transfer: gestational stage-specific gene delivery in mice; 1999, *Gene Therapy*, 6:1685-1694.
Vicat, et al., Muscle Transfection by Electroporation with High-Voltage and Short-Pulse Currents Provides High-Level and Long-Lasting Gene Expression; 2000, *Human Gene Therapy*, 11:909-916.
Wells, et al., Electroporation-enhanced gene delivery in mammary tumors; 2000, *Gene Therapy*, 7:541-547.
Zhang, et al., Surgical Procedures for Intravascular Delivery of Plasmid DNA to Organs, 2002, *Methods in Enzymology*; 346:125-133.
Zhang, et al., High Levels of Foreign Gene Expression in Hepatocytes after Tail Vein Injections of Naked Plasmid DNA, 1999, *Human Gene Therapy*; 10:1735-1737.

(Continued)

*Primary Examiner*—Michael C. Wilson
(74) *Attorney, Agent, or Firm*—Kyle D. Yesland

(57) ABSTRACT

The present invention provides for methods of producing transgenic avians which may include delivering a heterologous nucleic acid to oviduct tissue of an avian wherein the nucleic acid enters a cell of the oviduct tissue and is expressed.

32 Claims, No Drawings

OTHER PUBLICATIONS

Zhang, et al., Efficient Expression of Naked DNA Delivered Intraarterially to Limb Muscles of Nonhuman Primates, 2001, *Human Gene Therapy*; 12:427-438.

Zhang, et al., Expression of Naked Plasmid DNA Injected into the Afferent and Efferent Vessels of Rodent and Dog Livers, 1997, *Human Gene Therapy*; 8:1763-1772.

Zhang, et al., Long-term expression of human alpha 1-antitrypsin gene in mouse liver achieved by intravenous administration of plasmid DNA using a hydrodynamics-based procedure, 2000, *Gene Therapy*; 7:1344-1349.

Budker, et al., Naked DNA delivered intraportally expresses efficiently in hepatocytes, 1996, *Gene Therapy*; 7: 593-598.

Sikes, et al., In vivo Gene Transfer Into Rabbit Thyroid Follicular Cells By Direct DNA Injection, 1994, *Human Gene Therapy*; 5: 837-844.

Hickman, et al., Gene expression following direct injection of DNA into liver, 1994, *Human Gene Therapy*; 5:1477-1483.

Meyer, et al., Intratracheal gene delivery to the mouse airway: characterization of plasmid DNA expression and pharmacokinetics, 1995, *Gene Therapy*, 2:450-460.

Danko, et al., Pharmacological enhancement of in vivo foreign gene expression in muscle, 1994, *Gene Therapy*, 1:114-121.

* cited by examiner

IN VIVO TRANSFECTION IN AVIANS

The present application is a continuation-in-part of U.S. patent application Ser. No. 10/790,455 filed Mar. 1, 2004, now abandoned, the disclosure of which is incorporated by reference in its entirety herein and claims priority from U.S. Provisional Patent Application Ser. No. 60/469,527, filed May 9, 2003, the disclosure of which is incorporated by reference in its entirety herein.

FIELD OF THE INVENTION

The present invention relates to the field of biotechnology, and more specifically to the field of avian genome modification. Disclosed herein are methods for the generation of genetically transformed avians.

BACKGROUND

The present invention is based, in part, on the discovery that transgenic avians may be produced by in vivo transfection. In particular, the present invention provides methods for producing transgenic avians by delivering nucleic acid (e.g., heterologous nucleic acid) to tissue, such as the oviduct tissue, of a live avian. The present invention provides for, among other things, producing transgenic avians by in vivo electroporation of avian tissue and by applying nucleic acid to avian tissue under pressure.

Transgenic technology to convert animals into "bioreactors" for the production of specific proteins or other substances of pharmaceutical interest (Gordon et al., 1987, *Biotechnology* 5: 1183-1187; Wilmut et al, 1990, *Theriogenology* 33: 113-123) offers significant advantages over more conventional methods of protein production by gene expression. Recombinant nucleic acid molecules have been engineered and incorporated into transgenic animals so that an expressed heterologous protein may be joined to a protein or peptide that allows secretion of the transgenic expression product into milk or urine, from which the protein may then be recovered. These procedures, however, may require lactating animals, with the attendant costs of maintaining individual animals or herds of large species, such as cows, sheep, or goats.

Historically, transgenic animals have been produced mostly by microinjection of the fertilized egg. The pronuclei of fertilized eggs are microinjected in vitro with heterologous DNA or hybrid DNA molecules. The microinjected fertilized eggs are then transferred to the genital tract of a pseudopregnant female (e.g., Krimpenfort et al., U.S. Pat. No. 5,175,384).

One system that holds potential is the avian reproductive system. The production of an avian egg begins with formation of a large yolk in the ovary of the hen. The unfertilized oocyte or ovum is positioned on top of the yolk sac. After ovulation, the ovum passes into the infundibulum of the oviduct where it is fertilized, if sperm are present, and then moves into the magnum of the oviduct which is lined with tubular gland cells. These cells secrete the egg-white proteins, including ovalbumin, lysozyme, ovomucoid, conalbumin and ovomucin, into the lumen of the magnum where they are deposited onto the avian embryo and yolk. The hen oviduct offers outstanding potential as a protein bioreactor because of the high levels of protein production, the promise of proper folding and post-translation modification of the target protein, the ease of product recovery, and the shorter developmental period of chickens compared to other potential animal species.

Various techniques have been used in efforts to create transgenic chickens expressing heterologous proteins in the oviduct.

Bosselman et al. in U.S. Pat. No. 5,162,215 describes a method for introducing a replication-defective retroviral vector into a pluripotent stem cell of an unincubated chick embryo, and further describes chickens whose cells express a heterologous vector nucleic acid sequence. Such retroviral vectors have significant limitations, for example, only relatively small fragments of nucleic acid can be inserted into the vectors precluding, in most instances, the use of large portions of the regulatory regions or introns of a genomic locus which can be useful in obtaining significant levels of heterologous protein expression. Additionally, retroviral vectors may be inappropriate for generating transgenics for the production of pharmaceuticals due to safety and regulatory issues.

In addition, previously described methods of producing transgenic avians may not always allow for the targeting of nucleic acid of interest to the desired tissue in the avian, for example, the oviduct tissue. Further, many techniques currently available for producing a transgenic chicken require the time necessary for a chicken to develop from a blastoderm to egg laying maturity.

What is needed are methods of introducing large segments of nucleic acid into avian cells and methods for the targeting nucleic acid to specific tissue in the avian for example, the oviduct tissue. Further, what is needed are methods of producing transgenic avians for which a prolonged time necessary to achieve egg-laying maturity is not required.

SUMMARY

The present invention relates to methods of producing transgenic avians and to transgenic avians and their eggs. Provided for are methods of introducing large nucleic acid segments, for example, large DNA segments present on plasmids, into avians, for example, avians of egg bearing age. Furthermore, the present invention provides for the specific targeting of certain tissue within avians, for example, specific targeting of the oviduct tissue.

In one aspect of the present invention, there are provided methods of producing transgenic avians which include locally delivering nucleic acid (e.g., heterologous nucleic acids) to certain tissue of avians, for example, to the oviduct tissue of avians. In this aspect of the invention, the nucleic acid enters a cell of the oviduct tissue (e.g., tubular gland cell) and is expressed. In a particularly useful embodiment, the nucleic acid integrates into the genome of the cell to produce a transgene.

In one aspect of the invention, the nucleic acid is delivered under pressure to oviduct tissue (e.g., oviduct tissue cells) of the avian. In one embodiment, the pressure is hydrostatic pressure. In another embodiment, the pressure is provided by injection of a solution comprising the nucleic acid into a blood vessel. For example, the injection may be an intravenous injection or may be an intraarterial injection. In one embodiment, the nucleic acid is delivered to the lumen of the oviduct of the avian.

In one aspect of the invention, nucleic acid is delivered to oviduct tissue (e.g., oviduct tissue cells) by electroporation, for example, in vivo electroporation. Procedures for electroporation are well known in the art and may be accomplished by standard techniques known to practitioners of ordinary skill.

The present invention may be employed for the transfection of any egg laying animal. The invention is particularly useful for the transfection of avians including, but not limited to, chicken, quail, turkey, duck, goose, pheasants, parrots, finches, hawks, crows and ratites including ostrich, emu or cassowary. In one useful embodiment, the avians are prepubertal hens or mature hens.

In accordance with the present invention, the nucleic acid to be transfected into the avian may be in a solution, for example, a physiologically acceptable solution. In one embodiment, the nucleic acid is DNA. For example, the nucleic acid may be circular DNA molecules. The nucleic acid may be a vector. In one embodiment, the vector is an expression construct.

In one embodiment of the invention, the nucleic acid comprises an attB site. Typically, in the embodiment of the invention where the nucleic acid comprises an attB site, integrase is delivered to the cell of the oviduct tissue before, during or after the transfection. In one embodiment, the integrase is encoded on a nucleic acid which is cotransfected with the nucleic acid of interest.

In a particularly useful aspect of the present invention, a polypeptide encoded by a coding sequence of the nucleic acid is present in egg white of eggs laid by transgenic avians produced according to methods disclosed herein. In one useful embodiment, the polypeptide is a pharmaceutical composition. In one embodiment, the pharmaceutical composition is a light chain or a heavy chain of an antibody, for example a human antibody. In another embodiment, the pharmaceutical composition is a cytokine, for example, interferon.

Any combination of features described herein are included within the scope of the present invention provided that the features included in any such combination are not mutually inconsistent. Such combinations will be apparent based on this specification and on the knowledge of one of ordinary skill in the art.

Definitions

For convenience, definitions of certain terms employed in the specification, examples, and appended claims are collected here.

As used in this specification and the appended claims, the singular forms "a," "an" and "the" include plural references unless the content clearly dictates otherwise. Thus, for example, reference to "a nucleic acid" includes a mixture of two or more nucleic acids.

The term "avian" as used herein refers to any species, subspecies or race of organism of the taxonomic class ava, such as, but not limited to chicken, turkey, duck, goose, quail, pheasants, parrots, finches, hawks, crows and ratites including ostrich, emu and cassowary. The term includes the various known strains of Gallus gallus, or chickens, (for example, White Leghorn, Brown Leghorn, Barred-Rock, Sussex, New Hampshire, Rhode Island, Australorp, Minorca, Amrox, California Gray), as well as strains of turkeys, pheasants, quails, duck, ostriches and other poultry commonly bred in commercial quantities. It also includes an individual avian organism in all stages of development, including embryonic and fetal stages. The term "avian" also may denote "pertaining to a bird", such as "an avian (bird) cell."

The term "nucleic acid" as used herein includes any natural or synthetic linear and sequential array (e.g., polymer) of nucleotides or nucleosides, for example cDNA, genomic DNA, MRNA, tRNA, oligonucleotides, oligonucleosides and derivatives thereof. For ease of discussion, such nucleic acids may be collectively referred to herein as "constructs," "plasmids," or "vectors." The term "nucleic acid" further includes modified or derivatized nucleotides and nucleosides such as, but not limited to, halogenated nucleotides such as, but not only, 5-bromouracil, and derivatized nucleotides such as biotin-labeled nucleotides.

The terms "polynucleotide," "oligonucleotide," and "nucleic acid sequence" may be used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin are suggested by the terms described above.

As used herein the terms "peptide," "polypeptide" and "protein" refer to a polymer of amino acids in a serial array, linked through peptide bonds. A "peptide" typically is a polymer of at least two to about 30 amino acids linked in a serial array by peptide bonds. The term "polypeptide" includes proteins, protein fragments, protein analogues, oligopeptides and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or noncovalently linked to labeling moieties.

A "pharmaceutical" or a "pharmaceutical composition" is any composition which may be useful as a therapeutic, alone or in combination with one or more other substances.

The terms "recombinant nucleic acid" and "recombinant DNA" as used herein refer to combinations of at least two nucleic acid sequences that are not naturally found in a eukaryotic or prokaryotic cell. The nucleic acid sequences may include, but are not limited to, nucleic acid vectors, gene expression regulatory elements, origins of replication, suitable gene sequences that when expressed confer antibiotic resistance, protein-encoding sequences and the like. The term "recombinant polypeptide" is meant to include a polypeptide produced by recombinant DNA techniques. A recombinant polypeptide may be distinct from a naturally occurring polypeptide either in its location, purity or structure.

The term "gene" or "genes" as used herein refers to nucleic acid sequences that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes". The term "gene product" refers to an RNA or protein that is encoded by the gene. "Endogenous gene products" are RNAs or proteins encoded by endogenous genes. "Heterologous gene products" are RNAs or proteins encoded by "foreign, heterologous or exogenous genes" and are, therefore, not naturally expressed in the cell.

The term "expressed" or "expression" as used herein refers to the transcription from a gene to give an RNA nucleic acid molecule at least complementary in part to a region of one of the two nucleic acid strands of the gene which is expressed. The term "expressed" or "expression" as used herein may also include the translation from an RNA molecule to give a protein, a polypeptide or a portion thereof.

The term "promoter" as used herein refers to the DNA sequence that determines the site of transcription initiation by an RNA polymerase.

The term "coding region" as used herein refers to a continuous linear arrangement of nucleotides which may be translated into a polypeptide. A full length coding region is translated into a full length protein; that is, a complete protein as would be translated in its natural state absent any post-translational modifications. A full length coding region may also include any leader protein sequence or any other region of the protein that may be excised naturally from the translated protein.

The terms "vector" or "nucleic acid vector" as used herein refer to a natural or synthetic single or double stranded plasmid or viral nucleic acid molecule (RNA or DNA) that can be transfected or transformed into cells and replicate independently of, or within, the host cell genome. The term "expression vector" as used herein refers to a nucleic acid vector that comprises a transcription regulatory region operably linked to a site wherein is, or can be, inserted, a nucleotide sequence to be transcribed and, optionally, to be expressed, for instance, but not limited to, a sequence coding at least one polypeptide.

The term "transfection" as used herein refers to the process of inserting a nucleic acid into a host cell.

The terms "recombinant cell" and "genetically transformed cell" refer to a cell comprising a combination of nucleic acid segments not found in a single cell with each other in nature. A new combination of nucleic acid segments can be introduced into an organism using a wide array of nucleic acid manipulation techniques available to those skilled in the art. The recombinant cell may harbor a vector that is extragenomic, i.e, that does not covalently insert into the cellular genome, including a non-nuclear (e.g., mitochondrial) genome(s). A recombinant cell may further harbor a vector or a portion thereof that is intragenomic, i.e., covalently incorporated within the genome of the recombinant cell.

As used herein, a "transgenic avian" is any avian, as defined above, including the chicken and quail, in which one or more of the cells of the avian contain heterologous nucleic acid introduced by manipulation, such as by transgenic techniques. A recombinant DNA molecule may be integrated within a chromosome, or it may be extrachromosomally replicating DNA.

The terms "chimeric animal" or "mosaic animal" are used herein to refer to animals in which the recombinant gene is found, or in which the recombinant is expressed, in some but not all cells of the animal. The term "tissue-specific chimeric animal" indicates that the recombinant gene is present or expressed in some tissues but not others.

As used herein, the term "transgene" means a nucleic acid sequence that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout).

The term "cytokine" as used herein refers to any secreted polypeptide that affects a function of cells and modulates an interaction between cells in the immune, inflammatory or hematopoietic response. A cytokine includes, but is not limited to, monokines and lymphokines. Examples of cytokines include, but are not limited to, interferon $\alpha 2b$, Interleukin-1 (IL-1), Interleukin-6 (IL-6), Interleukin-8 (IL-8), Tumor Necrosis Factor-$\alpha$(TNF-$\alpha$) and Tumor Necrosis Factor $\beta$(TNF-$\beta$).

The term "antibody" as used herein refers to polyclonal and monoclonal antibodies and fragments thereof, and immunologic binding equivalents thereof. Antibodies may include, but are not limited to polyclonal antibodies, monoclonal antibodies (MAbs), humanized or chimeric antibodies, single chain antibodies, FAb fragments, F(Ab')$_2$ fragments, fragments produced by a FAb expression library, anti-idiotypic (anti-Id) antibodies, and epitope-binding fragments of any of the above.

The term "immunoglobulin polypeptide" as used herein refers to a constituent polypeptide of an antibody or a polypeptide derived therefrom. An "immunological polypeptide" may be, but is not limited to, an immunological heavy or light chain and may include a variable region, a diversity region, joining region and a constant region or any combination, variant or truncated form thereof. The term "immunological polypeptides" further includes single-chain antibodies comprised of, but not limited to, an immunoglobulin heavy chain variable region, an immunoglobulin light chain variable region and optionally a peptide linker.

A "nucleic acid", a "nucleic acid of interest" or a "nucleic acid fragment of interest" may be a trait-producing sequence, by which it is meant a sequence conferring a non-native trait upon the cell in which the protein encoded by the trait-producing sequence is expressed. The term "non-native" when used in the context of a trait-producing sequence means that the trait produced is different than one would find in an unmodified organism which can mean that the organism produces relatively high amounts of a natural substance in comparison to an unmodified organism, or produces a non-natural substance. For example, the genome of a bird could be modified to produce proteins not normally produced in birds such as, for instance, human or mouse antibodies, human cytokines, etc. Other useful traits include disease resistance, meat flavor, animal size, and the like.

A nucleic acid or nucleic acid fragment of interest may additionally be a "marker nucleic acid" or expressed as a "marker polypeptide". Marker genes encode proteins that can be easily detected in transformed cells and are, therefore, useful in the study of those cells. Examples of suitable marker genes include $\beta$-galactosidase, green or yellow fluorescent proteins, enhanced green fluorescent protein, chloramphenicol acetyl transferase, luciferase, and the like. Such regions may also include those 5' noncoding sequences involved with initiation of transcription and translation, such as the enhancer, TATA box, capping sequence, CAAT sequence, and the like.

The term "transformed" as used herein refers to a heritable alteration in a cell resulting from the uptake of nucleic acid, for example, heterologous DNA.

Techniques useful for isolating and characterizing the nucleic acids and proteins of the present invention are well known to those of skill in the art and standard molecular biology and biochemical manuals may be consulted to select suitable protocols without undue experimentation. See, for example, *Sambrook* et al, 1989, "Molecular Cloning: A Laboratory Manual", 2nd ed., Cold Spring Harbor, the content of which is herein incorporated by reference in its entirety.

Abbreviations

Abbreviations which may be used in the present specification include the following: aa which means amino acid(s); bp which means base pair(s); cm which means centimeter (s); G which means gauge, h which means hours; kb which means kilobase; IU which means infectious units; mg which means milligram; ug which means microgram; psi which means pound per square inch; sec which means seconds; V which means volts; and msec which means milliseconds.

DETAILED DESCRIPTION

The present invention is based, in part, on the discovery that transgenic avians may be produced by in vivo transfection. In particular, the present invention provides methods for producing transgenic avians by delivering nucleic acid (e.g., heterologous nucleic acid) to tissue, such as the oviduct tissue, of a live avian. For example, transgenic avians may be produced by in vivo electroporation of avian tissue. In another example, in vivo transfection may be accomplished by applying nucleic acid to avian tissue under pressure thereby transfecting the tissue. Though the present invention is particularly useful for accomplishing in vivo transfection, methods disclosed herein are also useful to effect or facilitate virus transduction of avian tissue.

Avian tissue which may be transfected according to the present invention includes, without limitation, oviduct tissue. For example, tissue that may be transfected according to the present methods include, without limitation, the magnum, the ovaries, the infundibulum, and the isthmus.

The present methods may be used for the in vivo introduction of nucleic acid (e.g., heterologous nucleic acid) in any avian or any animal capable of laying an egg including, but not limited to, chicken, quail, duck, turkey, goose, pheasants, parrots, finches, hawks, crows and ratites including ostrich, emu and cassowary. In one aspect of the invention, the present methods are believed to be very useful for the in vivo introduction of nucleic acid into chicken, quail and duck. In one embodiment, the present methods are particularly useful for the in vivo introduction of nucleic acid into chicken.

In one embodiment of the present invention, nucleic acid enters cells of the avian, for example, cells comprising oviduct tissue. Typically, the nucleic acid is expressed in the recipient cells to produce a heterologous polypeptide. In one embodiment, an expressed heterologous polypeptide is deposited in egg white produced in the avians. In this case, without wishing to limit the invention to any theory or mechanism of operation, it is believed that upon transfection, the nucleic acid enters cells of the oviduct (e.g., tubular gland cells) and may incorporate into the genome of the cells. Subsequently, a coding region of the nucleic acid is expressed to produce a recombinant protein which is excreted into the lumen of the oviduct along with egg white proteins excreted from oviduct cells (e.g., tubular gland cells).

In vivo transfection of avian tissue may be performed on adult avians or on immature avians. In one embodiment, an immature avian is subject to steroid hormone treatment prior to in vivo transfection. An immature avian can be classified as an avian from hatchling to seventeen weeks of age. The steroid treatment may include administration of a hormone, or combination of hormones, which provide for a transiently increased proliferation of cells in the magnum of the immature avian. Hormones that may be administered include, without limitation, estrogen, progesterone, testosterone and related hormones. In one embodiment, estrogen is administered to the immature avian. In another embodiment, estrogen is administered to the immature avian in conjunction with progesterone or testosterone. Estrogen can be in any useful form. For example, estrogen may be in the form of estrone, estradiol or diethylstilbestrol (DES). Doses can be any useful amount. For example, a useful does range for DES is about 0.1 mg per kilogram of body weight to about 10 mg per kilogram of body weight once per day. The hormone may be administered, for example, injected, with any useful adjuvant such as vegetable oil. Further useful aspects of hormone induction in immature avians are readily apparent and well known to those skilled in the art.

In one useful embodiment, transfection is accomplished by the delivery of nucleic acid to tissue of an avian wherein the nucleic acid is under pressure. Typically, although not exclusively, the delivery of the nucleic acid to tissue by pressure is accomplished with the nucleic acid in a solution. In one embodiment, the solution is applied to the tissue with pressure exerted between the solution and the tissue. That is, an application of force is present between the solution and the tissue. The pressure may be any useful amount of positive pressure. The pressure may be in a range of about 0.001 psi to 200 psi, for example, in a range of about 0.05 psi to about 40 psi (e.g., about 0.1 psi to about 15 psi).

In one embodiment, the nucleic acid solution is applied to the tissue under hydrostatic or hydrodynamic pressure. For example, nucleic acid in solution may be applied to avian tissue, for example oviduct tissue (e.g, tissue of the magnum), wherein pressure is exerted from the weight of the solution. In another embodiment, the pressure may be provided by an instrument such as a syringe or any other such useful device.

In one embodiment of the present invention, transfection of an avian is accomplished by delivering a nucleic acid (e.g., heterologous nucleic acid) solution to avian tissue through a blood vessel. For example, nucleic acid may be delivered through an artery or a vein supplying blood to avian tissue, for example, oviduct tissue. In a particularly useful embodiment, the nucleic acid solution is provided to the tissue through the blood vessel under pressure.

For the methods of in vivo avian transfection disclosed herein, the tissue to be transfected may be surgically exposed, for example, removed wholly or in part from the avian, prior to the transfection. However, exposing or removing the tissue prior to transfection is not required. In a case where exposure of the tissue to be transfected is desired, the avian may be prepared for surgery by methods known in the field avian surgery. After preparation, an incision may be made in the bird in the vicinity of the tissue to be transfected. In the case of transfecting oviduct tissue, a vertical incision may be made in the skin of the avian on the left side of the abdominal cavity beginning at the junction of the sternal rib to the breastbone and running parallel to the breastbone. In this case, the muscle layer directly below the skin incision may be cut following the incision line made in the skin. The fat layer may be pulled away from the site of the incision, for example, pulled away toward the bird's left side. The peritoneal membrane may be incised exposing the reproductive tract. At this point, the reproductive tract may be eternalized. Preferably, if externalized, the reproductive tract is handled in a gentle manner. In one useful embodiment, the first or second loop of the magnum is stabilized by techniques known in the field of avian surgery and a catheter is slowly introduced into one or more oviductal arteries such as the anterior oviductal, inferior, superior and middle uterine artery and the artery is gently occluded. In one embodiment the artery is occluded above and below the catheter site. In another embodiment, the artery is occluded on the side of the catheter distal to the oviduct tissue.

Typically, a nucleic acid solution is injected into the blood vessel in a manner which results in an application of positive pressure between the nucleic acid solution and the tissue to be transfected. The present invention contemplates the employment of any useful amount of pressure. For example, the pressure may range from an amount which slightly distends the tissue exposed to the pressure to an amount of pressure less than that required to rupture the tissue. Any mechanical device useful for such injection may be employed in the present invention. For example a syringe, may be used. Other methods for introduction of the nucleic acid solution into a blood vessel, for example, an artery in a manner which applies positive pressure to the tissue which the nucleic acid solution comes in contact with are contemplated, such as the use of hydrostatic or hydrodynamic pressure. In one embodiment, where the blood vessel is occluded above and below the site of catheter insertion, the occlusion proximal to the tissue to be transfected (e.g., oviduct tissue) may be removed resulting in a large and rapid flow of nucleic acid solution to the tissue to be transfected.

A period of time after exposure of the tissue to be transfected to the nucleic acid solution, the blood vessel is unblocked. The period of time between injection and unblocking of the blood vessel may range from about one second to about 24 hours. For example, the period of time may be in a range of about one minute to about one hour. In one embodiment, the period of time between injection and unblocking of the blood vessel is about two minutes to about 6 minutes, for example, about three minutes.

The oviduct may be returned to the abdominal cavity and the fat layer positioned to cover the reproductive tract. Both the muscle and skin incisions may be closed utilizing simple continuous interlocking stitches. After surgery, the hen may be allowed to recover with free access to both feed and water.

Transfection may be performed by applying the nucleic acid to oviduct tissue inside the lumen of the oviduct. This may be achieved by any useful technique. In one embodiment, oviduct tissue is exposed surgically as described above. After exposure of the oviduct, a loop of the magnum, for example, the first loop of the magnum, is stabilized and the oviduct is occluded above and below the site where a hollow needle, such as a 20 gauge needle, is introduced into the loop of the magnum. A nucleic acid solution is injected into the lumen through the needle until expansion of the lumen is detected. A period of time after the injection the occlusions are removed. The period of time between injection and removal of the occlusions may range from about one second to about 24 hours. For example, the period of time may be in a range of about one minute to about one hour. In one embodiment, the period of time between removal of the occlusions is about two minutes to about 6 minutes, for example, about three minutes.

The application of the nucleic acid solution to avian tissue by force or pressure may be accomplished by any useful technique. For example, the nucleic acid solution may be propelled onto the tissue in the form of a mist, or a stream or in a spray.

It is not required that the nucleic acid be in solution when being delivered to avian tissue in accordance with the present invention. For example, the nucleic acid may be in a substantially dry form such as a precipitate which is delivered to the avian tissue (e.g., oviduct tissue) by force. For example, the nucleic acid may be delivered to avian tissue by a gene gun. In such a case the nucleic acid may be associated with a carrier, for example microspheres.

In vivo transfection of avian tissue (e.g., oviduct tissue) may be accomplished by in vivo electroporation. In one embodiment, the avian tissue (e.g., oviduct tissue) to be electroporated is exposed surgically prior to electroporation. In one embodiment, after exposure of the oviduct, a loop of the magnum, for example, the first loop of the magnum, is stabilized and the oviduct is occluded above and below the site where a 20 gauge needle is introduced into the loop of the magnum. A nucleic acid solution may be injected into the lumen through the needle. In one embodiment, a volume of nucleic acid solution sufficient to distend the lumen is injected into the lumen. In another embodiment, a volume of nucleic acid solution sufficient to substantially fill the lumen is injected into the lumen; however, filling of the lumen, or substantial filling of the lumen, with the nucleic acid solution may not be required for the present electroporation methods. An electrical current can be applied to the occluded area of the magnum which holds the injected nucleic acid. Any voltage useful for electroporating avian tissue may be used. For example, the voltage may range from about 10 V to about 10,000, for example, about 20 V to about 600 V. In one particularly useful embodiment, the voltage ranges from about 100 V to about 250 V. The current may be applied to the tissue for any useful amount of time. For example, the current may be applied for a period of time in a range of about 0.001 msec to about 1 h. For example, the current may be applied for about 0.01 msec to about 1 sec (e.g., about 0.1 msec to about 0.5 sec). In one particularly useful embodiment the current is applied for about 10 to about 20 msec. The current may be administered any number of useful times. In one embodiment, the current is administered between 1 and about 1,000,000 times per site of administration. For example, the current may be administered between 1 and about 100,000 times (e.g., 1 to about 1000 times) per site of administration. In one particularly useful embodiment, the current is administered between 1 and about 100 times per site of administration, for example between 4 and 24 times per site of administration.

The nucleic acid may be, for example, and without limitation, a plasmid or construct that incorporates a region capable of expressing a protein or selected polypeptide in a recipient cell. The nucleic acid may comprise elements that regulate or are necessary for the transcription or translation of nucleic acid (e.g., heterologous nucleic acid) in the transfected tissue of the avian. The nucleic acid may be in a physiologically acceptable solution and may further comprise agents to facilitate the uptake of the nucleic acid by the recipient cells of the oviduct such as, but not limited to, polyanionic substances such as PEI, lipofectin, liposomes and the like.

Any useful concentration of nucleic acid may be used in the present methods. For example, the nucleic acid may be present in the solution in a range of about 1 ug per ml to an amount where the solution is saturated with the nucleic acid. In one embodiment, the nucleic acid is present in solution in a range of about 10 ug per ml to about 10 mg per ml, for example, about 0.1 mg per ml to about 2 mg per ml.

The nucleic acid solution may include salts such as sodium chloride at a useful concentration, buffers such as a phosphate buffer at a useful concentration or sugars such as glucose at a useful concentration. Any useful volume of nucleic acid solution may be used in accordance with the present methods. In one embodiment, a useful volume is about 0.05 ml to about 200 ml. For example, a useful volume may be about 0.5 ml to about 50 ml (e.g., about 1 ml to about 20 ml).

Any tissue of an avian may be transfected using the present methods as is obvious to a practitioner of ordinary skill in the field. For example, testicular tissue or oviduct tissue may be transfected by methods of the present invention. The nucleic acid transfected into the avian tissue (e.g., oviduct tissue) may include a nucleotide region which encodes a useful biological product such as, a pharmaceutical composition.

The present invention can be useful for the production of many biological molecules such as hormones including cytokines (i.e., secreted polypeptides that affect a function of cells and modulates an interaction between cells in an immune, inflammatory or hematopoietic response) antibodies and other useful pharmaceutical molecules which include polypeptides. Cytokines includes, but are not limited to, monokines and lymphokines. Examples of cytokines include, but are not limited to, interferon α2b, Interleukin-1 (IL-1), Interleukin-6 (IL-6), Interleukin-8 (IL-8), Tumor Necrosis Factor-α(TNF-α) and Tumor Necrosis Factor β(TNF-β), antibodies such as polyclonal and monoclonal antibodies and fragments thereof, and immunologic binding equivalents thereof. Antibodies may include, but are not limited to polyclonal antibodies, monoclonal antibodies (MAbs), humanized or chimeric antibodies, single chain antibodies, FAb fragments, F(Ab')$_2$ fragments, fragments produced by a FAb expression library, anti-idiotypic (anti-Id) antibodies, and epitope-binding fragments thereof. The methods of the present invention can also be useful for producing immunoglobulin polypeptides which are constituent polypeptides of an antibody or a polypeptide derived therefrom. An "immunological polypeptide" may be, but is not limited to, an immunological heavy or light chain and may include a variable region, a diversity region, joining region and a constant region or any combination, variant or truncated form thereof. Immunological polypeptides also include single-chain antibodies comprised of, but not limited to, an immunoglobulin heavy chain variable region, an immunoglobulin light chain variable region and optionally a peptide linker.

Certain specific examples of pharmaceutical compositions which are contemplated for production as disclosed herein include, with out limitation, Factor VIII (e.g., Recombinate®, Bioclate®, Kogenate®, Helixate® (Centeon), B-domain deleted Factor VIII (e.g., ReFacto®), Factor VIIa (e.g., NovoSeven®), Factor IX (e.g., Benefix®), anticoagulant; recombinant hirudin (e.g., Revasc®, Refludan®) Alteplase, tPA (e.g., Activase®), Reteplase, tPA, tPA-3 of 5 domains deleted, Ecokinase®, Retavase®, Rapilysin®, insulin (e.g., Humulin®, Novolin®, Insuman®) insulin lispro (e.g., Humalog®, Bio Lysprol, Liprolog®), insulin Aspart, iNovoRapid®, insulin glargine, long-acting insulin analog (e.g., Lantus®), rhGH (e.g., Protropin®, Humatrope®, Nutropin®, BioTropin®, Genotropin®, Norditropin®, Saizen®, Serostim®), glucagons (e.g., Glucagen®), TSH (e.g., Thyrogen®, Gonal F®, Puregon®), follitropin-beta FSH (e.g., Follistim®), EPO (e.g., Epogen®, Procrit®, Neorecormon®), GM-CSF (e.g., Leukine®, Neupogen®), PDGH (e.g., Regranex®), IFN alpa2a (e.g., Roferon A®), INF-apha (e.g., Infergen®), IFN alpa2b (e.g., Intron A®, Alfatronol®, Virtron®), ribavirin & INF-alpha 2b (e.g., Robetron®) INF-beta 1b, differs from h protein by C17 to S (e.g., Betaferon®), IFN-beta 1a (e.g., Avonex®, Rebif®), IFN-gamma1b (e.g., Actimmune®), IL-2 (e.g., Proleukin®) rIL-11 (e.g., Neumega®), rHBsAg (e.g., Recombivax®), Combination vaccine containing HBsAgn as one component (e.g., Comvax®, Tritarix®, Twinrix®, Primavax®, Procomax®), OspA, a lipoprotein found on the surface of B burgoeri (e.g., Lymerix®), murine MAb directed against t-lymphocyte antigen CD3 (e.g., Orthoclone OKT3®), murine MAb directed against TAG-72, tumor-associated glycoprotein (e.g., OncoScint CR/OV®), FAb fragments derived from chimeric MAb, directed against platelet surface receptor GPII(b)/III(a) (e.g., ReoPro®), murine MAb fragment directed against tumor-associated antigen CA125 (e.g., Indimacis®), murine MAb fragment directed against human carcinoembryonic antigen, CEA (e.g., CEA-scan®), murine MAb fragment directed against human cardiac myosin (e.g., MyoScint®), murine MAb fragment directed against tumor surface antigen PSMA (e.g., ProstaScint®), murine MAb fragments (FAb/FAb2 mix) directed against HMW-MAA (e.g., Tacnemab®), murine MAb fragment (FAb) directed against carcinoma-associated antigen (e.g., Verluma®), MAb fragments (FAb) directed against NCA 90, a surface granulocyte nonspecific cross reacting antigen (e.g., LeukoScan®), chimeric MAb directed against CD20 antigen found on surface of B lymphocytes (e.g., Rituxan®), humanized MAb directed against the alpha chain of the IL2 receptor (e.g., Zenapax®), chimeric MAb directed against the alpha chain of the IL2 receptor (e.g., Simulect®), chimeric MAb directed against TNF-alpha (e.g., Remicade®), humanized MAb directed against an epitope on the surface of respiratory synctial virus (e.g., Synagis®), humanized MAb directed against HER 2, i.e., human epidermal growth factor receptor 2 (e.g., Herceptin®), human MAb directed against cytokeratin tumor-associated antigen (e.g., Humaspect®), anti-CTLA4, chimeric MAb directed against CD 20 surface antigen of B lymphocytes (e.g., Mabthera®), domase-alpha DNAse (e.g., Pulmozyme®), beta glucocerebrosidase (e.g., Cerezyme®), TNF-alpha (e.g., Beromun®), IL-2-diptheria toxin fusion protein that targets cells displaying a surface IL-2 receptor (e.g., Ontak®), TNFR-lgG fragment fusion protein (e.g., Enbrel®), Laronidase, Recombinant DNA enzyme, (e.g., Aldurazyme®), Alefacept, Amevive®, Darbepoetin alfa (Colony stimulating factor) (e.g., Aranesp®), Tositumomab and iodine 1 131 tositumomab, murine MAb, Bexxar®, Alemtuzumab, Campath®, Rasburicase, Elitek®), Agalsidase beta, Fabrazyme®, FluMist®, Teriparatide, Parathyroid hormone derivative (e.g., Forteo®), Enfuvirtide Fuzeon®, Adalimumab (lgG1) (e.g., Humira®), Anakinra, Biological modifier (e.g., Kineret®), nesiritide, Human B-type natriuretic peptide (hBNP) (e.g., Natrecor®), Pegfilgrastim, Colony stimulating factor (e.g., Neulasta®), ribavarin and peg Intron A (e.g., Rebetron®), Pegvisomant, PEGylated human growth hormone receptor antagonist, (e.g., Somavert®), recombinant activated protein C (e.g., Xigris®), Omalizumab, Immunoglobulin E (lgE) blocker (e.g., Xolair®) and lbritumomab tiuxetan (murine MAb) (e.g., Zevalin®).

The present invention contemplates the use of certain compositions and methods disclosed in U.S. patent application Ser. No. 10/790,455, now abandoned, and in U.S. patent application Ser. No. 10/811,136, now abandoned, the disclosures of which are incorporated in their entirety herein by reference, for use in combination with the present methods. For example, and without limitation, integrase or nucleic acid which encodes integrase may be used in combination with the present invention. In addition, other agents which facilitate transfection or chromosome integration disclosed in the patents and patent applications incorporated by reference herein may be used in combination with the present methods.

Certain gene expression controlling regions, such as promoters, may be included in nucleic acid which is transfected into avian tissue in accordance with the present methods. Any useful gene expression controlling region or coding region may be used in accordance with the present invention. Examples include, without limitation, those gene expression controlling regions or coding regions disclosed in U.S. patent application Ser. No. 10/790,455, now abandoned, U.S. patent application Ser. No. 10/811,136, now abandoned, U.S. patent application Ser. No. 09/173,864, now issued U.S. Pat. No. 6,730,822 U.S. patent application Ser. No. 09/654,293, now issued U.S. Pat. No. 7,049,480 U.S. patent application Ser. No. 09/998,716, now issued U.S. Pat. No. 6,875,588, U.S. patent application Ser. No. 10/099,663, now issued U.S. Pat. No. 7,135,562, and U.S. patent application Ser. No. 10/733,042. The disclosures of each of these patent applications is incorporated herein in their entirety by reference.

The methods of the invention are useful for expressing nucleic acid sequences that are optimized for expression in avian cells and which encode desired polypeptides or derivatives and fragments thereof. Derivatives include, for instance, polypeptides with conservative amino acid replacements, that is, those within a family of amino acids that are related in their side chains. These families are commonly known as acidic, basic, nonpolar, and uncharged polar amino acid families. Phenylalanine, tryptophan, and tyrosine are sometimes classified jointly as aromatic amino acids and other groupings are known in the art (see, for example, "Biochemistry", 2nd ed, L. Stryer, ed., W. H. Freeman & Co., 1981). Peptides in which more than one replacement is made can readily be tested for activity in the same manner as derivatives with a single replacement, using conventional polypeptide activity assays (e.g., for enzymatic or ligand binding activities).

If the nucleic acid molecules are transfected into a recipient chicken cell, the sequence of a nucleic acid insert to be expressed can be optimized for chicken codon usage. This may be determined from the codon usage of at least one, and preferably more than one, protein expressed in a chicken cell according to well known principles. For example, in the chicken the codon usage could be determined from the nucleic acid sequences encoding the proteins such as lysozyme, ovalbumin, ovomucin and ovotransferrin of chicken. Optimization of the sequence for codon usage can elevate the level of translation in avian eggs.

The present invention further relates to methods for gene expression by avian cells from nucleic acid vectors, and transgenes derived therefrom, that include more than one polypeptide-encoding region wherein, for example, a first polypeptide-encoding region can be operatively linked to an avian promoter and a second polypeptide-encoding region is operatively linked to an Internal Ribosome Entry Sequence (IRES). It is contemplated that the first polypeptide-encoding region, the IRES and the second polypeptide-encoding region of a recombinant DNA of the present invention may be arranged linearly, with the IRES operably positioned immediately 5' of the second polypeptide-encoding region. This nucleic acid construct, when inserted into the genome of an avian cell or a bird and expressed therein, will generate individual polypeptides that may be post-translationally modified and combined in the white of a hard shell bird egg. Alternatively, the expressed polypeptides may be isolated from an avian egg and combined in vitro.

The invention, therefore, includes methods for producing multimeric proteins including immunoglobulins, such as antibodies, and antigen binding fragments thereof. Thus, in one embodiment of the present invention, the multimeric protein is an immunoglobulin, wherein the first and second heterologous polypeptides are immunoglobulin heavy and light chains respectively. Illustrative examples of this and other aspects of the present invention for the production of heterologous multimeric polypeptides in avian cells are fully disclosed in U.S. patent application Ser. No. 09/877,374, and U.S. patent application Ser. No. 10/251,364, the disclosures of each of which is incorporated herein by reference in their entirety.

Accordingly, the invention further provides immunoglobulin and other multimeric proteins that have been produced by transgenic avians of the invention.

The present invention is further illustrated by the following examples, which are provided by way of illustration and should not be construed as limiting. The contents of all references, published patents and patents cited throughout the present application are hereby incorporated by reference in their entireties.

It will be apparent to those skilled in the art that various modifications, combinations, additions, deletions and variations can be made in the present invention without departing from the scope or spirit of the invention. For instance, features illustrated or described as part of one embodiment can be used in another embodiment to yield a still further embodiment. It is intended that the present invention covers such modifications, combinations, additions, deletions and variations as come within the scope of the appended claims and their equivalents.

EXAMPLE 1

Expression of Luciferase and Green Fluorescent Protein in Transgenic Chickens Produced by In Vivo Transfection by Electroporation in the Presence of Integrase Encoding DNA Plasmid DNA encoding luciferase, plasmid DNA encoding GFP, each also encoding an attB site, and plasmid DNA encoding φ C-31 integrase, the coding sequence of each plasmid operably linked to a CMV promoter, were prepared using a Qiagen endotoxin-free plasmid purification kit. Each of the plasmid preparations was suspended in 150 mM NaCl prior to use.

Five sexually mature hens (17-18 weeks) were prepared for surgery. After oviposition of an egg, each hen was anesthetized using isofluorane gas. The bird was placed in a supine position and feathers removed from the left abdominal and leg area. The surgical area was scrubbed with betadine and rinsed with 70% Alcohol. A surgical drape was placed over the bird with the surgical field exposed. A 5-7 cm vertical incision was made in the skin on the left side of the abdominal cavity beginning at the junction of the sternal rib to the breastbone and running parallel to the breastbone. The muscle layer directly below the skin incision was cut following the same lines as above. The fat layer was pulled leftward and the thin peritoneal membrane was punctured. The reproductive tract was located and gently externalized.

The first loop of the magnum was stabilized and the oviduct was gently occluded about 2-3 cm above and below the site where a 20 gauge needle was introduced into the loop. A solution comprising 100 ug/ml of plasmid encoding GFP, 400 ug/ml of plasmid encoding luciferase and 500 ug/ml of plasmid DNA encoding φ C-31 integrase was injected into the lumen through the needle substantially filling the lumen.

Electrical current was applied directly to, and to areas surrounding, the injection site. The voltage ranged from 100 V to 250 V and was applied for 10 to 20 msec. The current was administered 4 to 24 times per site.

The oviduct was returned to the abdominal cavity and the fat layer was manipulated so that it covered the entire reproductive tract. Both the muscle and skin incisions were closed utilizing simple continuous interlocking stitches and the hens were allowed to recover with free access to both feed and water. Two days later the hens were sacrificed and the electroporated tissue was examined for the presence of GFP or luciferase. Four of the five birds tested positive for luciferase production in the tissue of the magnum and three of the five birds tested positive for GFP in the tissue of the magnum.

EXAMPLE 2

Expression of Human Interferon Alpha in Transgenic Chickens Produced by In Vivo Transfection by Electroporation in the Presence of Integrase Encoding DNA Plasmid DNA which includes an attB site and encodes human interferon operably linked to a CMV promoter and plasmid DNA encoding φ C-31 integrase operably linked to a CMV promoter were prepared using a Qiagen endotoxin-free plasmid purification kit. Each plasmid DNA was suspended in 150 mM NaCl prior to use.

Two prepubertal hens, age approximately 14 weeks, were moved from 12 hours of light exposure per day to 18 hours of light exposure per day two days prior to the beginning of hormone induction. Hens were injected with 1.0 mg of diethylstilbestrol and 0.8 mg of progesterone each day for three days prior to electroporation, the day of electroporation and two days after the electroporation for a total of six days.

For each bird, the reproductive tract was surgically externalized as described in Example 1. The magnum was stabilized and a 20 G needle was introduced into the lumen. A solution comprising 200 ug/ml of plasmid encoding human interferon and 500 ug/ml of plasmid DNA encoding φ C-31 integrase was injected into the lumen through the needle until expansion of the lumen was detected. Electrical current was applied to 8-10 sites per bird. Voltage ranged from 150 V to 200 V for 10-20 msec with 16-24 pulses per site. The oviduct was returned to the abdominal cavity and the incisions were closed as described in Example 1. The hens were allowed to recover with free access to both feed and water. After hormone treatment was ceased, the birds were allowed to develop to sexual maturity.

Eggs were collected from the birds and the egg white was subjected to ELISA analysis for interferon. Both birds produced eggs in which human interferon was detected.

EXAMPLE 3

Expression of Human Interferon Alpha in Transgenic Chickens Produced by In Vivo Transfection by DNA Injection into an Artery DNA preparation: Plasmid DNA encoding human interferon alpha operably linked to either a CMV promoter or a 10 kilobase chicken ovomucoid promoter was prepared using a Qiagen endotoxin-free plasmid purification kit. 0.15 milligrams of each plasmid DNA was suspended in 2 ml of a 5% glucose solution.

Twenty eight adult chickens were transfected with DNA encoding human interferon alpha operably linked to a CMV promoter. Fourteen adult chickens were transfected with DNA encoding human interferon alpha operably linked to 10 kb chicken ovomucoid promoter. For each bird the following protocol was employed.

For each bird the reproductive tract was located and gently externalized as described in Example 1. The first or second loop of the magnum was stabilized and an oviductal artery such as the anterior oviductal, inferior, superior and middle uterine artery was located. A pediatric catheter was slowly introduced into the artery and the artery was gently occluded about 2-3 cm both below and above the catheter. The DNA solution was slowly injected into the artery. A few minutes after injection the catheter was removed and the artery was unblocked. The oviduct was returned to the abdominal cavity and the incisions were closed as described in Example 1. The hens were allowed to recover with free access to both feed and water.

Egg white from eggs laid after oviduct injection were analyzed for the presence of interferon by ELISA. Three of the twenty eight adult chickens transfected with plasmid DNA encoding human interferon alpha operably linked to a CMV promoter laid eggs with interferon present in the egg white. Six of the fourteen adult chickens transfected with plasmid DNA encoding human interferon alpha operably linked to a 10 kb chicken ovomucoid promoter laid eggs with interferon present in the egg white.

EXAMPLE 4

Expression of a Human Monoclonal Antibody in Transgenic Chickens Produced by In Vivo Transfection by Electroporation in the Presence of Integrase Encoding DNA Plasmid DNA which includes an attB site and encoding a human monoclonal antibody operably linked to an ovomucoid promoter and plasmid DNA encoding φ C-31 integrase operably linked to a CMV promoter were prepared using a Qiagen endotoxin-free plasmid purification kit. Each plasmid DNA was suspended in 150 mM NaCl prior to use.

Three prepubertal hens, age approximately 14 weeks, were moved from 12 hours of light exposure per day to 18 hours of light exposure per day 2 days prior to the beginning of hormone induction. Hens were injected with 1 mg of diethylstilbestrol and 0.8 mg of progesterone each day for three days prior to electroporation, the day of electroporation and two days after the electroporation treatment for a total of six days.

For each bird, the reproductive tract was surgically externalized as described in Example 1. The magnum was stabilized and a 20 G needle was introduced into the lumen. A solution comprising 200 ug/ml of plasmid encoding a human antibody and 500 ug/ml of plasmid DNA encoding φ C-31 integrase was injected into the lumen through the needle until expansion of the lumen was detected. Electrical current was applied to 8-10 sites per bird. Voltage ranged from 150 V to 200 V for 10-20 msec with 16-24 pulses per site. The oviduct was returned to the abdominal cavity and the incisions were closed as described in Example 1. The hens were allowed to recover with free access to both feed and water. After hormone treatment was ceased, the birds were allowed to develop to sexual maturity.

One of the four hens did not lay eggs. Eggs were collected from the remaining birds and the egg white was subjected to ELISA analysis for the human antibody. Antibody was detected in the egg white of two of the three hens analyzed.

EXAMPLE 5

Expression of Human Interferon Alpha in Transgenic Chickens Produced by Mature Lumen Injection Plasmid DNA encoding human interferon alpha operably linked to a CMV promoter was prepared using a Qiagen endotoxin-free plasmid purification kit. The plasmid DNA was suspended in 150 mM NaCl prior to use.

The reproductive tract of two adult hens was surgically externalized as described in Example 1. The magnum was stabilized and a 20 G needle was introduced into the lumen. A solution comprising 200 ug/ml of plasmid encoding human interferon alpha and in 5% PEI was injected into the lumen through the needle until expansion of the lumen was detected. The oviduct was returned to the abdominal cavity and the incisions were closed as described in Example 1. The hens were allowed to recover with free access to both feed and water Eggs were collected from the birds and the egg white was subjected to ELISA analysis for human interferon. Interferon was detected in the egg white of one of the two hens.

EXAMPLE 6

Expression of Human Interferon Alpha in Transgenic Chickens Produced by In Vivo Transfection by Electroporation Plasmid DNA encoding human interferon alpha operably linked to a CMV promoter is prepared using a Qiagen endotoxin-free plasmid purification kit. The DNA is suspended in 150 mM NaCl prior to use.

Twelve prepubertal hens, age approximately 14 weeks, are moved from 12 hours of light exposure per day to 18 hours of light exposure per day 2 days prior to the beginning of hormone induction. The hens are injected with 1 mg of diethylstilbestrol and 0.8 mg of progesterone each day for three days prior to electroporation, the day of electroporation and two days after the electroporation treatment for a total of six days.

For each bird, the reproductive tract is surgically externalized as described in Example 1. The magnum is stabilized and a 20 G needle is introduced into the lumen. 1 ml of a solution comprising 200 ug/ml of plasmid encoding human interferon is injected into the lumen through the needle. Electrical current is applied to 8-10 sites per bird. Voltage ranges from 150 V to 200 V for 10-20 msec with 16-24 pulses per site. The oviduct is returned to the abdominal cavity and the incisions are closed as described in Example 1. The hens are allowed to recover with free access to both feed and water. After hormone treatment is ceased, the birds are allowed to develop to sexual maturity.

Eggs are collected from the birds and the egg white is subjected to ELISA analysis for interferon. Eggs are produced in which interferon is detected by three of the twelve birds in the study.

EXAMPLE 7

Expression of a Monoclonal Antibody Directed Against the Alpha Chain of an IL-2 Receptor in Transgenic Chickens Produced by In Vivo Electroporation Plasmid DNA encoding a monoclonal antibody directed against the alpha chain of the IL-2 receptor operably linked to an avian lysozyme promoter is prepared using a Qiagen endotoxin-free plasmid purification kit. The DNA is suspended in 150 mM NaCl prior to use.

Eight prepubertal hens, age approximately 14 weeks, are moved from 12 hours of light exposure per day to 18 hours of light exposure per day 2 days prior to the beginning of hormone induction. The hens are injected with 1 mg of diethylstilbestrol and 0.8 mg of progesterone each day for three days prior to electroporation, the day of electroporation and 2 days after the electroporation treatment for a total of six days.

For each bird, the reproductive tract is surgically externalized as described in Example 1. The magnum is stabilized and a 20 G needle is introduced into the lumen. A solution comprising 200 ug/ml of plasmid encoding a monoclonal antibody directed against the alpha chain of the IL-2 receptor is injected into the lumen through the needle until expansion of the lumen is detected. Electrical current is applied to 8-10 sites per bird. Voltage ranges from 150 V to 200 V for 10-20 msec with 16-24 pulses per site. The oviduct is returned to the abdominal cavity and the incisions are closed as described in Example 1. The hens are allowed to recover with free access to both feed and water. After hormone treatment is ceased, the birds are allowed to develop to sexual maturity.

Eggs are collected from the birds and the egg white is subjected to ELISA analysis for monoclonal antibody directed against the alpha chain of the IL-2 receptor. Three of the eight birds produce eggs in which the monoclonal antibody is detected.

EXAMPLE 8

Expression of Human Erythropoietin in Transgenic Chickens Produced by Mature Lumen Injection Plasmid DNA encoding human EPO operably linked to an ovomucoid promoter is prepared using a Qiagen endotoxin-free plasmid purification kit. Each plasmid DNA is suspended in 150 mM NaCl prior to use.

The reproductive tract of seven adult hens is surgically externalized as described in Example 1. The magnum is stabilized and a 20 G needle is introduced into the lumen. A solution comprising 200 ug/ml of plasmid encoding a human EPO is injected into the lumen through the needle until expansion of the lumen is detected. The oviduct is returned to the abdominal cavity and the incisions are closed as described in Example 1. The hens are allowed to recover with free access to both feed and water Eggs are collected from the birds and the egg white is subjected to ELISA analysis for human EPO. Eggs are produced by two of the seven birds in which EPO is detected.

EXAMPLE 9

Expression of a MAb Directed Against CD 20 Surface Antigen of B Lymphocytes in Transgenic Chickens Produced by In Vivo Electroporation Plasmid DNA encoding a MAb directed against CD 20 surface antigen of B lymphocytes operably linked to an avian lysozyme promoter is prepared using a Qiagen endotoxin-free plasmid purification kit. The DNA is suspended in 150 mM NaCl prior to use.

Eight prepubertal hens, age approximately 14 weeks, are moved from 12 hours of light exposure per day to 18 hours of light exposure per day 2 days prior to the beginning of hormone induction. The hens are injected with 1 mg of diethylstilbestrol and 0.8 mg of progesterone each day for three days prior to electroporation, the day of electroporation and 2 days after the electroporation treatment for a total of six days.

For each bird, the reproductive tract is surgically externalized as described in Example 1. The magnum is stabilized and a 20 G needle is introduced into the lumen. A solution comprising 200 ug/ml of plasmid encoding a MAb directed against CD 20 surface antigen of B lymphocytes is injected into the lumen through the needle until expansion of the lumen is detected. Electrical current is applied to 8-10 sites per bird. Voltage ranges from 150 V to 200 V for 10-20 msec with 16-24 pulses per site. The oviduct is returned to the abdominal cavity and the incisions are closed as described in Example 1. The hens are allowed to recover with free access to both feed and water. After hormone treatment is ceased, the birds are allowed to develop to sexual maturity.

Eggs are collected from the birds and the egg white is subjected to ELISA analysis for a MAb directed against CD 20 surface antigen of B lymphocytes. Three of the eight birds produce eggs in which the monoclonal antibody is detected.

EXAMPLE 10

Expression of a Monoclonal Antibody Directed Against TNF-Alpha in Transgenic Chickens Produced by In Vivo Electroporation Plasmid DNA encoding a monoclonal antibody directed against TNF-alpha operably linked to a CMV promoter is prepared using a Qiagen endotoxin-free plasmid purification kit. The DNA is suspended in 150 mM NaCl prior to use.

Eight prepubertal hens, age approximately 14 weeks, are moved from 12 hours of light exposure per day to 18 hours of light exposure per day 2 days prior to the beginning of hormone induction. The hens are injected with 1 mg of diethylstilbestrol and 0.8 mg of progesterone each day for three days prior to electroporation, the day of electroporation and 2 days after the electroporation treatment.

For each bird, the reproductive tract is surgically externalized as described in Example 1. The magnum is stabilized and a 20 G needle is introduced into the lumen. A solution comprising 200 ug/ml of plasmid encoding a monoclonal antibody directed against TNF-alpha is injected into the lumen though the needle until expansion of the lumen is detected. Electrical current is applied to 8-10 sites per bird. Voltage ranges from 150 V to 200 V for 10-20 msec with 16-24 pulses per site. The oviduct is returned to the abdominal cavity and the incisions are closed as described in Example 1. The hens are allowed to recover with free access to both feed and water. After hormone treatment is ceased, the birds are allowed to develop to sexual maturity.

Eggs are collected from the birds and the egg white is subjected to ELISA analysis for antibodies directed against TNF-alpha. Eggs in which the human monoclonal antibody is detected are produced by two of the eight birds.

EXAMPLE 11

Expression of a Human CTLA4 Monoclonal Antibody in Transgenic Quail Produced by In Vivo Electroporation Plasmid DNA encoding a human CTLA4 monoclonal antibody operably linked to a CMV promoter is prepared using a Qiagen endotoxin-free plasmid purification kit. The DNA is suspended in 150 mM NaCl prior to use.

Ten adult quail are prepared for surgery and the reproductive tract is surgically externalized essentially as described in Example 1. The magnum is stabilized and a hollow needle is introduced into the lumen. A solution comprising 200 ug/ml of plasmid encoding a human CTLA4 antibody is injected into the lumen through the needle until expansion of the lumen is detected. Electrical current is applied to 8-10 sites per bird. Voltage ranges from 150 V to 200 V for 10-20 msec with 16-24 pulses per site. The oviduct is returned to the abdominal cavity and the incisions are closed essentially as described in Example 1. The birds are allowed to recover with free access to both feed and water. After hormone treatment is ceased, the birds are allowed to develop to sexual maturity.

Eggs are collected from each of the birds and the egg white is subjected to ELISA analysis for human CTLA4 antibody. Four of the ten birds produce eggs in which the monoclonal antibody is detected.

EXAMPLE 12

Expression of Human Erythropoietin in Transgenic Quail Produced by Mature Lumen Injection Plasmid DNA encoding human EPO operably linked to an ovomucoid promoter is prepared using a Qiagen endotoxin-free plasmid purification kit. Each plasmid DNA is suspended in 150 mM NaCl prior to use.

The reproductive tract of 14 adult quail is surgically externalized essentially as described in Example 1. The magnum is stabilized and a hollow needle is introduced into the lumen. A solution comprising 200 ug/ml of plasmid encoding a human EPO is injected into the lumen through the needle until expansion of the lumen is detected. The oviduct is returned to the abdominal cavity and the incisions are closed as described in Example 1. The quail are allowed to recover with free access to both feed and water Eggs are collected from the quail and the egg white of each is subjected to ELISA analysis for human EPO. Eggs are produced by three of the fourteen birds in which EPO is detected.

EXAMPLE 13

Expression of Human Interferon Alpha in Transgenic Ducks Produced by In Vivo Transfection by Electroporation Plasmid DNA encoding human interferon alpha is prepared using a Qiagen endotoxin-free plasmid purification kit. The DNA is suspended in 150 mM NaCl prior to use.

Sixteen prepubertal ducks are moved from 12 hours of light exposure per day to 18 hours of light exposure per day 2 days prior to the beginning of hormone induction. The ducks are injected with 1 mg of diethylstilbestrol and 0.8 mg of progesterone each day for three days prior to electroporation, the day of electroporation and two days after the electroporation treatment for a total of six days.

For each bird, the reproductive tract is surgically externalized essentially as described in Example 1. The magnum is stabilized and a 20 G needle is introduced into the lumen. 1.0 ml of a solution comprising 200 ug/ml of plasmid encoding human interferon is injected into the lumen through the needle. Electrical current is applied to 8-10 sites per bird. Voltage ranges from 150 V to 200 V for 10-20 msec with 16-24 pulses per site. The oviduct is returned to the abdominal cavity and the incisions are closed as described in Example 1. The ducks are allowed to recover with free access to both feed and water. After hormone treatment is ceased, the birds are allowed to develop to sexual maturity.

Eggs are collected from the birds and the egg white is subjected to ELISA analysis for Interferon. Eggs are produced in which the interferon is detected by four of the sixteen birds in the study.

EXAMPLE 14

Expression of Antibody Directed Against TNF-alpha in Transgenic Ducks Produced by Mature Lumen Injection Plasmid DNA encoding an antibody directed against TNF-alpha operably linked to an ovomucoid promoter is prepared using a Qiagen endotoxin-free plasmid purification kit. Each plasmid DNA is suspended in 150 mM NaCi prior to use.

The reproductive tract of eighteen adult ducks is surgically externalized essentially as described in Example 1. The magnum is stabilized and a 20 G needle is introduced into the lumen. A solution comprising 200 ug/ml of plasmid encoding an antibody directed against TNF-alpha is injected into the lumen through the needle until expansion of the lumen is detected. The oviduct is returned to the abdominal cavity and the incisions are closed as described in Example 1. The ducks are allowed to recover with free access to both feed and water.

Eggs are collected from the ducks and the egg white of each is subjected to ELISA analysis for antibody directed against TNF-alpha. Eggs are produced by three of the eighteen birds in which antibody is detected.

While this invention has been described with respect to various specific examples and embodiments, it is to be understood that the invention is not limited thereto and that it can be variously practiced with the scope of the following claims.

What is claimed is:

1. A method of producing a transgenic avian comprising delivering a nucleic acid solution under pressure to oviduct tissue of an avian by injecting the nucleic acid solution into an artery selected from the group consisting of anterior oviductal artery, inferior uterine artery, superior uterine artery, and middle uterine artery, wherein the nucleic acid enters a cell of the oviduct tissue and is expressed, thereby producing a transgenic avian.

2. The method of claim 1 wherein the avian is selected from the group consisting of chicken, quail, turkey, duck, goose, pheasants, parrots, finches, hawks, crows, ratites, ostrich, emu and cassowary.

3. The meted of claim 1 wherein the avian is selected from the group consisting of chicken, quail and duck.

4. The method of claim 1 wherein the avian is a chicken.

5. The method of claim 1 wherein the pressure is hydrostatic pressure or hydrodynamic pressure.

6. The method of claim 1 wherein the cell is a tubular gland cell.

7. The method of claim 1 wherein the artery is occluded.

8. The method of claim 1 wherein the nucleic acid is DNA.

9. The method of claim 1 wherein the nucleic acid is a circular molecule.

10. The method of claim 1 wherein an expression construct comprises the nucleic acid.

11. The method of claim 1 wherein the nucleic acid comprises an attB site.

12. The method of claim 1 wherein DNA encoding integrase is delivered to the cell of the oviduct tissue.

13. The method of claim 1 wherein a polypeptide encoded by a coding sequence of the nucleic acid is present in egg white produced by the transgenic avian.

14. The method of claim 13 wherein the polypeptide is a pharmaceutical.

15. The method of claim 14 wherein the pharmaceutical is a light chain or a heavy chain of an antibody.

16. The method of claim 15 wherein the antibody is a human antibody.

17. The method of claim 14 wherein the pharmaceutical is a cytokine.

18. The method of claim 14 wherein the pharmaceutical is selected from the group consisting of erythropoietin and interferon.

19. A method of producing a transgenic avian comprising delivering a nucleic acid solution under hydrostatic pressure to oviduct tissue of an avian by injecting the nucleic acid solution into an artery selected from the group consisting of anterior oviductal artery, inferior uterine artery, superior uterine artery, and middle uterine artery, wherein the nucleic acid enters a cell of the oviduct tissue and is expressed, thereby producing a transgenic avian.

20. The method of claim 19 wherein the avian is selected from the group consisting of chicken, quail, turkey, duck, goose, pheasants, parrots, finches, hawks, crows, ratites, ostrich, emu and cassowary.

21. The method of claim 19 wherein the avian is selected from the group consisting of chicken, quail and duck.

22. The method of claim 19 wherein the avian is a chicken.

23. The method of claim 19 wherein the nucleic acid comprises an attB site.

24. The method of claim 19 wherein DNA encoding integrase is delivered to the cell of the oviduct tissue.

25. The method of claim 19 wherein the cell is a tubular gland cell.

26. The method of claim 19 wherein the nucleic acid is a vector.

27. The method of claim 19 wherein an expression construct comprises the nucleic acid.

28. The method of claim 19 wherein a polypeptide encoded by a coding sequence of the nucleic acid is present in egg white produced by the transgenic avian.

29. The method of claim 28 wherein the polypeptide is a pharmaceutical.

30. The method of claim 29 wherein the pharmaceutical is a light chain or a heavy chain of an antibody.

31. The method of claim 29 wherein the pharmaceutical is a cytokine.

32. The method of claim 19 wherein the artery is occluded.

* * * * *